(12) United States Patent
Beerling et al.

(10) Patent No.: US 8,712,554 B2
(45) Date of Patent: Apr. 29, 2014

(54) INTEGRATED WIRE CARRIER FOR ELECTRODE ARRAY

(75) Inventors: Timothy Beerling, Los Angeles, CA (US); Chuladatta Thenuwara, Castaic, CA (US)

(73) Assignee: Advanced Bionics, Valencia, CA (US)

( * ) Notice: Subject to any disclaimer, the term of this patent is extended or adjusted under 35 U.S.C. 154(b) by 691 days.

(21) Appl. No.: 12/506,964

(22) Filed: Jul. 21, 2009

(65) Prior Publication Data

US 2011/0022145 A1 Jan. 27, 2011

(51) Int. Cl.
*A61N 1/00* (2006.01)

(52) U.S. Cl.
USPC ........... 607/137; 607/115; 607/116; 607/119; 607/122; 600/379

(58) Field of Classification Search
USPC .......... 607/119, 122, 116, 137, 115; 600/379; 606/129
See application file for complete search history.

(56) References Cited

U.S. PATENT DOCUMENTS

| | | |
|---|---|---|
| 5,437,632 A | 8/1995 | Engelson |
| 5,470,322 A | 11/1995 | Horzewski et al. |
| 5,476,497 A | 12/1995 | Mower et al. |
| 5,573,520 A | 11/1996 | Schwartz et al. |
| 5,630,839 A | 5/1997 | Corbett et al. |
| 5,653,742 A | 8/1997 | Parker et al. |
| 5,762,630 A | 6/1998 | Bley et al. |
| 5,800,500 A | 9/1998 | Spelman et al. |
| 5,999,859 A | 12/1999 | Jolly |
| 6,048,338 A | 4/2000 | Larson et al. |
| 6,119,044 A * | 9/2000 | Kuzma .......................... 607/137 |
| 6,125,302 A | 9/2000 | Kuzma |
| 6,321,125 B1 | 11/2001 | Kuzma |

(Continued)

FOREIGN PATENT DOCUMENTS

| | | |
|---|---|---|
| EP | 1341578 B1 | 4/2002 |
| EP | 1604626 A2 | 12/2005 |

(Continued)

OTHER PUBLICATIONS

He, Bo et al., Surface Texture effect on Friction of a Microtextured Polydimethylsiloxane, Tribology Letters, vol. 31, No. 3, Aug. 12, 2008; pp. 1-11.

(Continued)

*Primary Examiner* — Michael Kahelin
*Assistant Examiner* — Mallika D Fairchild
(74) *Attorney, Agent, or Firm* — Steven L. Nichols; Van Cott, Bagley, Cornwall & McCarthy P.C.

(57) ABSTRACT

A cochlear lead includes a plurality electrodes forming an electrode array configured to stimulate an auditory nerve from within a cochlea; a lead body connected to the electrode array; a plurality of wires passing through the lead body and connecting to the plurality of electrodes; an integrated wire carrier extending between an exit of the wires from the lead body and a first electrode in the electrode array, the integrated wire carrier comprising a cavity along its longitudinal axis configured to contain the plurality of wires and shape the plurality of wires into a wire bundle in which the plurality of wires passing through the integrated wire carrier are substantially parallel to the longitudinal axis of the integrated wire carrier; and a flexible body encapsulating the integrated wire carrier and the wires.

20 Claims, 6 Drawing Sheets

(56) References Cited

U.S. PATENT DOCUMENTS

| | | |
|---|---|---|
| 6,368,316 B1 | 4/2002 | Jansen et al. |
| 6,421,569 B1 * | 7/2002 | Treaba et al. ............... 607/137 |
| 6,428,489 B1 | 8/2002 | Jacobsen et al. |
| 6,475,209 B1 | 11/2002 | Larson et al. |
| 6,516,230 B2 * | 2/2003 | Williams et al. ............ 607/116 |
| 6,556,873 B1 | 4/2003 | Smits |
| 6,562,021 B1 | 5/2003 | Derbin et al. |
| 6,604,283 B1 | 8/2003 | Kuzma |
| 6,757,970 B1 | 7/2004 | Kuzma et al. |
| 6,858,680 B2 | 2/2005 | Gunatillake et al. |
| 6,887,235 B2 | 5/2005 | O'Connor et al. |
| 6,968,238 B1 | 11/2005 | Kuzma |
| 6,999,821 B2 | 2/2006 | Jenney et al. |
| 7,047,081 B2 | 5/2006 | Kuzma |
| 7,050,858 B1 | 5/2006 | Kuzma et al. |
| 7,063,708 B2 | 6/2006 | Gibson et al. |
| 7,066,931 B2 | 6/2006 | O'Connor et al. |
| 7,115,183 B2 | 10/2006 | Larson et al. |
| 7,146,227 B2 | 12/2006 | Dadd et al. |
| 7,239,923 B1 | 7/2007 | Tockman et al. |
| 7,269,461 B2 | 9/2007 | Dadd et al. |
| 7,272,449 B2 | 9/2007 | Dadd et al. |
| 7,315,763 B2 * | 1/2008 | Kuzma et al. ............... 607/137 |
| 7,319,906 B2 | 1/2008 | Kuzma et al. |
| 7,328,072 B2 | 2/2008 | Milojevic et al. |
| 7,389,148 B1 | 6/2008 | Morgan |
| 7,403,823 B1 | 7/2008 | Kroll et al. |
| 7,451,000 B2 | 11/2008 | Gibson et al. |
| 7,540,865 B2 | 6/2009 | Griffin et al. |
| 7,571,012 B2 | 8/2009 | Gibson |
| 7,742,827 B2 | 6/2010 | Lenarz et al. |
| 2002/0029074 A1 | 3/2002 | Treaba et al. |
| 2003/0040684 A1 | 2/2003 | Soukup |
| 2003/0045921 A1 | 3/2003 | Dadd et al. |
| 2003/0093139 A1 | 5/2003 | Gibson et al. |
| 2003/0181967 A1 | 9/2003 | Dadd et al. |
| 2004/0030376 A1 | 2/2004 | Gibson et al. |
| 2004/0078057 A1 | 4/2004 | Gibson |
| 2004/0127968 A1 | 7/2004 | Kuzma et al. |
| 2005/0234535 A1 | 10/2005 | Risi et al. |
| 2006/0089569 A1 | 4/2006 | Soukup |
| 2006/0235500 A1 | 10/2006 | Gibson |
| 2007/0073371 A1 | 3/2007 | Dadd et al. |
| 2007/0127745 A1 | 6/2007 | Gibson et al. |
| 2007/0162098 A1 * | 7/2007 | Risi et al. ................... 607/137 |
| 2007/0173683 A1 | 7/2007 | Harrison et al. |
| 2008/0027527 A1 | 1/2008 | Kuzma et al. |
| 2008/0077049 A1 | 3/2008 | Hirshman |
| 2008/0109011 A1 | 5/2008 | Thenuwara et al. |
| 2008/0269864 A1 | 10/2008 | Dadd et al. |
| 2009/0030483 A1 | 1/2009 | Risi et al. |
| 2009/0043358 A1 | 2/2009 | Dadd et al. |
| 2009/0043369 A1 | 2/2009 | Radeloff |
| 2009/0043370 A1 | 2/2009 | Gibson et al. |
| 2009/0165921 A1 | 7/2009 | Kaiser |
| 2009/0312769 A1 | 12/2009 | Dadd et al. |
| 2010/0057180 A1 | 3/2010 | Gibson |
| 2010/0106232 A1 | 4/2010 | Dadd et al. |
| 2010/0204768 A1 | 8/2010 | Jolly et al. |
| 2010/0287770 A1 | 11/2010 | Dadd et al. |
| 2011/0016710 A1 | 1/2011 | Dadd |
| 2011/0022145 A1 | 1/2011 | Beerling et al. |

FOREIGN PATENT DOCUMENTS

| | | |
|---|---|---|
| EP | 1604626 A3 | 12/2005 |
| EP | 1189560 B1 | 3/2006 |
| EP | 1604626 B1 | 12/2008 |
| EP | 2042137 A1 | 4/2009 |
| EP | 2209520 A1 | 7/2010 |
| WO | 9306698 | 4/1993 |
| WO | 9710784 | 3/1997 |
| WO | 0071063 | 11/2000 |
| WO | 0182848 A2 | 11/2001 |
| WO | 0228473 | 4/2002 |
| WO | 0228474 | 4/2002 |
| WO | 0230507 | 4/2002 |
| WO | 0232498 | 4/2002 |
| WO | 0243623 | 6/2002 |
| WO | 02094334 | 11/2002 |
| WO | 03049658 | 6/2003 |
| WO | 2004002570 | 1/2004 |
| WO | 2004004413 | 1/2004 |
| WO | 2007002879 A1 | 3/2007 |
| WO | 2007027879 | 3/2007 |
| WO | 2009065127 A1 | 5/2009 |
| WO | 2009065171 A1 | 5/2009 |
| WO | 2009079704 A1 | 7/2009 |
| WO | 2010015016 | 2/2010 |
| WO | 2010015017 | 2/2010 |
| WO | 2010091237 A2 | 8/2010 |
| WO | 2010091237 A3 | 8/2010 |
| WO | 2011011160 A2 | 1/2011 |

OTHER PUBLICATIONS

Stover, Timo et al., "Microstructured Cochlear implant electrodes," Subproject T1 of Collaborative Research Center 599; pp. 1-2; Feb. 7, 2011.

Lenarz, Thomas et al., "Nerve-Electrode Interface," Subproject D2 of Collaborative Research Center 599; pp. 1-2; Feb. 7, 2011.

Reuter G. et al., "Fine tuning of cochlear implant materials—cell interactions by femtosecond laser microstructuring." European Cells and Materials vol. 13. Suppl. 3, 2007 (p. 10).

Rebscher et al, Strategies to Improve Electrode Positioning and Safety in Cochlear Implants, IEEE Trans Biomed Eng, 46(3) 340-352, 1999.

Kha et al., Stiffness Properties of Nucleus Standard Straight and Contour Electrode Arrays, Med and Eng Phys 26 677-685, 2004.

* cited by examiner

INTEGRATED WIRE CARRIER FOR ELECTRODE ARRAY

BACKGROUND

In human hearing, hair cells in the cochlea respond to sound waves and produce corresponding auditory nerve impulses. These nerve impulses are then conducted to the brain and perceived as sound.

Hearing loss, which may be due to many different causes, is generally of two types: conductive and sensorineural. Conductive hearing loss typically occurs where the normal mechanical pathways for sound to reach the hair cells in the cochlea are impeded, for example, from damage to the ossicles. Conductive hearing loss may often be helped by using conventional hearing aids that amplify sounds so that acoustic information can reach the cochlea and the hair cells. Some types of conductive hearing loss are also treatable by surgical procedures.

Many people who are profoundly deaf, however, have sensorineural hearing loss. This type of hearing loss can arise from the absence or the destruction of the hair cells in the cochlea which then no longer transduce acoustic signals into auditory nerve impulses. Individuals with sensorineural hearing loss may be unable to derive significant benefit from conventional hearing aid systems alone, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural deafness, cochlear implant systems, or cochlear prostheses, have been developed that can bypass the hair cells located in the cochlea by presenting electrical stimulation directly to the auditory nerve fibers. This leads to the perception of sound in the brain and provides at least partial restoration of hearing function. Most of these cochlear prosthesis systems treat sensorineural deficit by stimulating the ganglion cells in the cochlea directly using an implanted electrode or lead that has an electrode array. Thus, a cochlear prosthesis operates by directly stimulating the auditory nerve cells, bypassing the defective cochlear hair cells that normally transduce acoustic energy into electrical activity in the connected auditory nerve cells.

Prior to stimulating the nerve cells, the electronic circuitry and the electrode array of the cochlear prosthesis separate acoustic signals into a number of parallel channels of information, each representing a narrow band of frequencies within the perceived audio spectrum. Ideally, each channel of information should be conveyed selectively to a subset of auditory nerve cells that normally transmit information about that frequency band to the brain. Those nerve cells are arranged in an orderly tonotopic sequence, from the highest frequencies at the basal end of the cochlear spiral to progressively lower frequencies towards the apex.

A cochlear implant system typically comprises both an external unit that receives and processes ambient sound waves and a cochlear implant that receives data from the external unit and uses that data to directly stimulate the auditory nerve. A cochlear implant is a surgically implanted electronic device having electrodes that reside in the cochlea of a patient's ear and provides a sense of sound to the patient who is profoundly deaf or severely hard of hearing. In a typical cochlear implant, a microphone receives sound and converts it into electrical signals. These electrical signals are transmitted to a processor. Typically, the processor is implanted in the patient's body and is connected to an array of electrode contacts which are implanted within one of the cochlear ducts, such as the scala tympani. The processor receives the electrical signals and transmits them down a bundle of wires to specific electrode contacts. The electrode contacts then generate electrical fields which stimulate the auditory nerve. This provides the patient with a sense of hearing.

One challenge in constructing and surgically inserting a cochlear device is managing the delicate wires which connect the processor to the electrode contacts. To minimize the trauma to the patient, the wires have a small diameter. However, during manufacturing and insertion, extra precautions are required to maintain the organization of the wire bundle and to protect the wire bundle from kinking. Damage to the wires can result in decrease performance or failure of the cochlear implant.

BRIEF DESCRIPTION OF THE DRAWINGS

The accompanying drawings illustrate various embodiments of the principles described herein and are a part of the specification. The illustrated embodiments are merely examples and do not limit the scope of the claims.

Throughout the drawings, identical reference numbers designate similar, but not necessarily identical, elements.

DETAILED DESCRIPTION

As mentioned above, individuals with hearing loss can be assisted by a number of hearing devices, including cochlear implants. To place the lead of a cochlear implant, the distal (or apical) portion of a cochlear lead is pushed through an opening into the cochlea. The distal portion of the lead is typically constructed out of biocompatible silicone, platinum-iridium wires, and platinum electrodes. This gives the distal portion of the lead the flexibility to curve around the helical interior of the cochlea. During manufacturing, the proper management of wires which pass through the lead and connect to electrodes avoids damage to the wire or flawed assembly of the lead.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "an embodiment," "an example," or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

The electrode array to be implanted in the scala tympani typically comprises a thin, elongated, flexible carrier containing several longitudinally disposed and separately connected stimulating electrode contacts, conventionally numbering about 6 to 30. Such an electrode array is pushed into the scala tympani duct in the cochlea, typically to a depth of about 13-30 mm via a cochleostomy or via a surgical opening made in the round window at the basal end of the duct.

In use, the cochlear electrode array delivers electrical current into the fluids and tissues immediately surrounding the individual electrode contacts to create transient potential gradients that, if sufficiently strong, cause the nearby auditory nerve fibers to generate action potentials. The auditory nerve fibers branch from cell bodies located in the spiral ganglion, which lies in the modiolus, adjacent to the inside wall of the scala tympani. The density of electrical current flowing through volume conductors such as tissues and fluids tends to be highest near the electrode contact that is the source of such current. Consequently, stimulation at one contact site tends to selectively activate those spiral ganglion cells and their auditory nerve fibers that are closest to that contact site.

Figure 1:
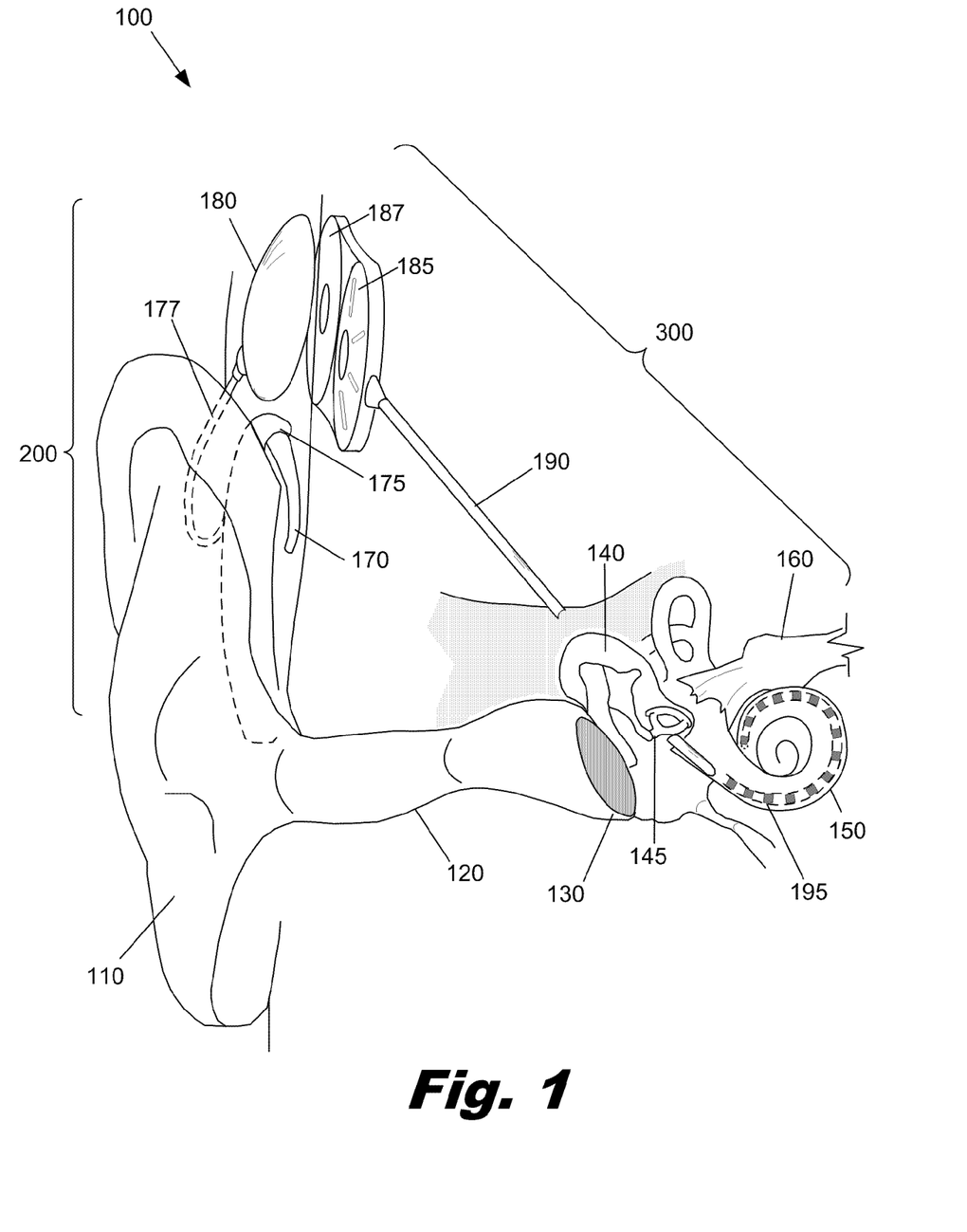
FIG. 1 is an illustrative diagram showing a cochlear implant system in use, according to one embodiment of principles described herein.

FIG. 1 is a diagram showing one illustrative embodiment of a cochlear implant system (100) having a cochlear implant (300) with an electrode array (195) that is surgically placed within the patient's auditory system. Ordinarily, sound enters the external ear, or pinna, (110) and is directed into the auditory canal (120) where the sound wave vibrates the tympanic membrane (130). The motion of the tympanic membrane is amplified and transmitted through the ossicular chain (140), which consists of three bones in the middle ear. The third bone of the ossicular chain (140), the stirrup (145), contacts the outer surface of the cochlea (150) and causes movement of the fluid within the cochlea. Cochlear hair cells respond to the fluid-borne vibration in the cochlea (150) and trigger neural electrical signals that are conducted from the cochlea to the auditory cortex by the auditory nerve (160).

As indicated above, the cochlear implant (300) is a surgically implanted electronic device that provides a sense of sound to a person who is profoundly deaf or severely hard of hearing. In many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide no benefit to persons suffering from complete sensorineural hearing loss.

Unlike hearing aids, the cochlear implant (300) does not amplify sound, but works by directly stimulating any functioning auditory nerve cells inside the cochlea (150) with electrical impulses representing the ambient acoustic sound. Cochlear prosthesis typically involves the implantation of electrodes into the cochlea. The cochlear implant operates by direct electrical stimulation of the auditory nerve cells, bypassing the defective cochlear hair cells that normally transduce acoustic energy into electrical energy.

External components (200) of the cochlear implant system can include a Behind-The-Ear (BTE) unit (175), which contains the sound processor and has a microphone (170), a cable (177), and a transmitter (180). The microphone (170) picks up sound from the environment and converts it into electrical impulses. The sound processor within the BTE unit (175) selectively filters and manipulates the electrical impulses and sends the processed electrical signals through the cable (177) to the transmitter (180). The transmitter (180) receives the processed electrical signals from the processor and transmits them to the implanted antenna (187) by electromagnetic transmission. In some cochlear implant systems, the transmitter (180) is held in place by magnetic interaction with the underlying antenna (187).

The components of the cochlear implant (300) include an internal processor (185), an antenna (187), and a cochlear lead (190) having an electrode array (195). The internal processor (185) and antenna (187) are secured beneath the user's skin, typically above and behind the pinna (110). The antenna (187) receives signals and power from the transmitter (180). The internal processor (185) receives these signals and performs one or more operations on the signals to generate modified signals. These modified signals are then sent along a number of delicate wires which pass through the cochlear lead (190) are individually connected to the electrodes in the electrode array (195). The electrode array (195) is implanted within the cochlea (150) and provides electrical stimulation to the auditory nerve (160).

The cochlear implant (300) stimulates different portions of the cochlea (150) according to the frequencies detected by the microphone (170), just as a normal functioning ear would experience stimulation at different portions of the cochlea depending on the frequency of sound vibrating the liquid within the cochlea (150). This allows the brain to interpret the frequency of the sound as if the hair cells of the basilar membrane were functioning properly.

Figure 2:
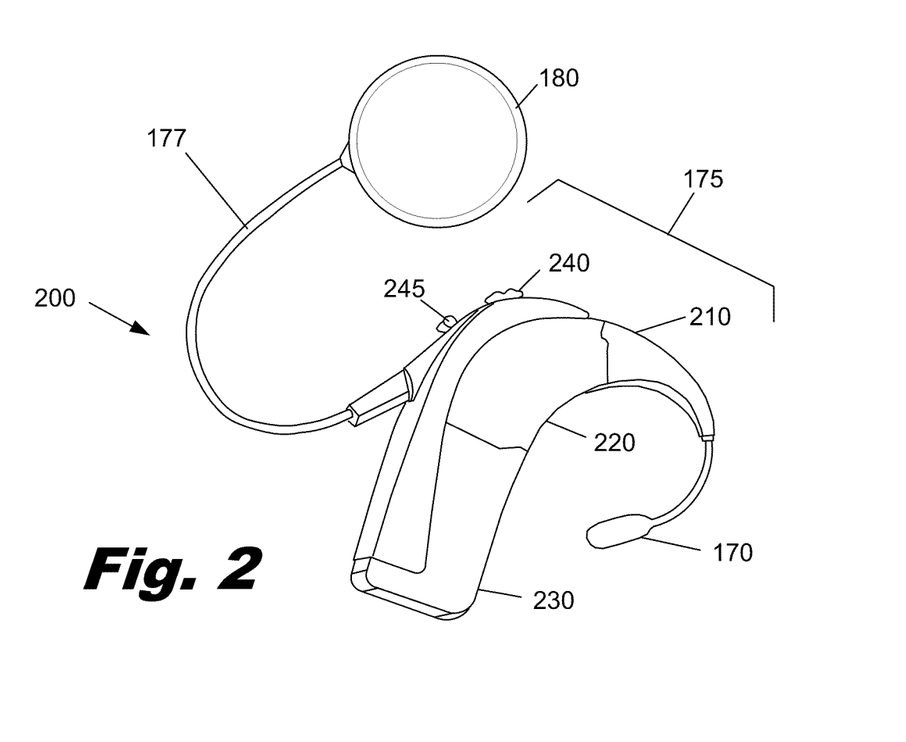
FIG. 2 is a diagram showing external components of an illustrative cochlear implant system, according to one embodiment of principles described herein.

FIG. 2 is an illustrative diagram showing a more detailed view of the external components (200) of one embodiment of a cochlear implant system. External components (200) of the cochlear implant system include a BTE unit (175), which comprises a microphone (170), an ear hook (210), a sound processor (220), and a battery (230), which may be rechargeable. The microphone (170) picks up sound from the environment and converts it into electrical impulses. The sound processor (220) selectively filters and manipulates the electrical impulses and sends the processed electrical signals through a cable (177) to the transmitter (180). A number of controls (240, 245) adjust the operation of the processor (220). These controls may include a volume switch (240) and program selection switch (245). The transmitter (180) receives the processed electrical signals from the processor (220) and transmits these electrical signals and power from the battery (230) to the cochlear implant by electromagnetic transmission.

Figure 3:
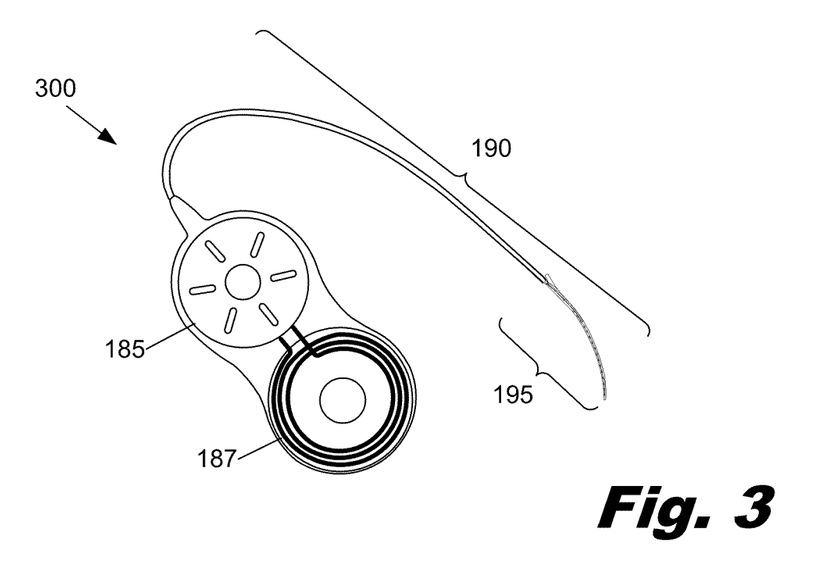
FIG. 3 is a diagram showing the internal components of an illustrative cochlear implant system, according to one embodiment of principles described herein.

FIG. 3 is an illustrative diagram showing one embodiment of a cochlear implant (300), including an internal processor (185), an antenna (187), and a cochlear lead (190) having an electrode array (195). The cochlear implant (300) is surgically implanted such that the electrode array (195) is internal to the cochlea, as shown in FIG. 1. The internal processor (185) and antenna (187) are secured beneath the user's skin, typically above and behind the pinna (110), with the cochlear lead (190) connecting the internal processor (185) to the electrode array (195) within the cochlea. As discussed above, the antenna (187) receives signals from the transmitter (180)

and sends the signals to the internal processor (185). The internal processor (185) modifies the signals and passes them along the appropriate wires to activate one or more of the electrodes within the electrode array (195). This provides the user with sensory input that is a representation of external sound waves sensed by the microphone (170).

Figure 4:
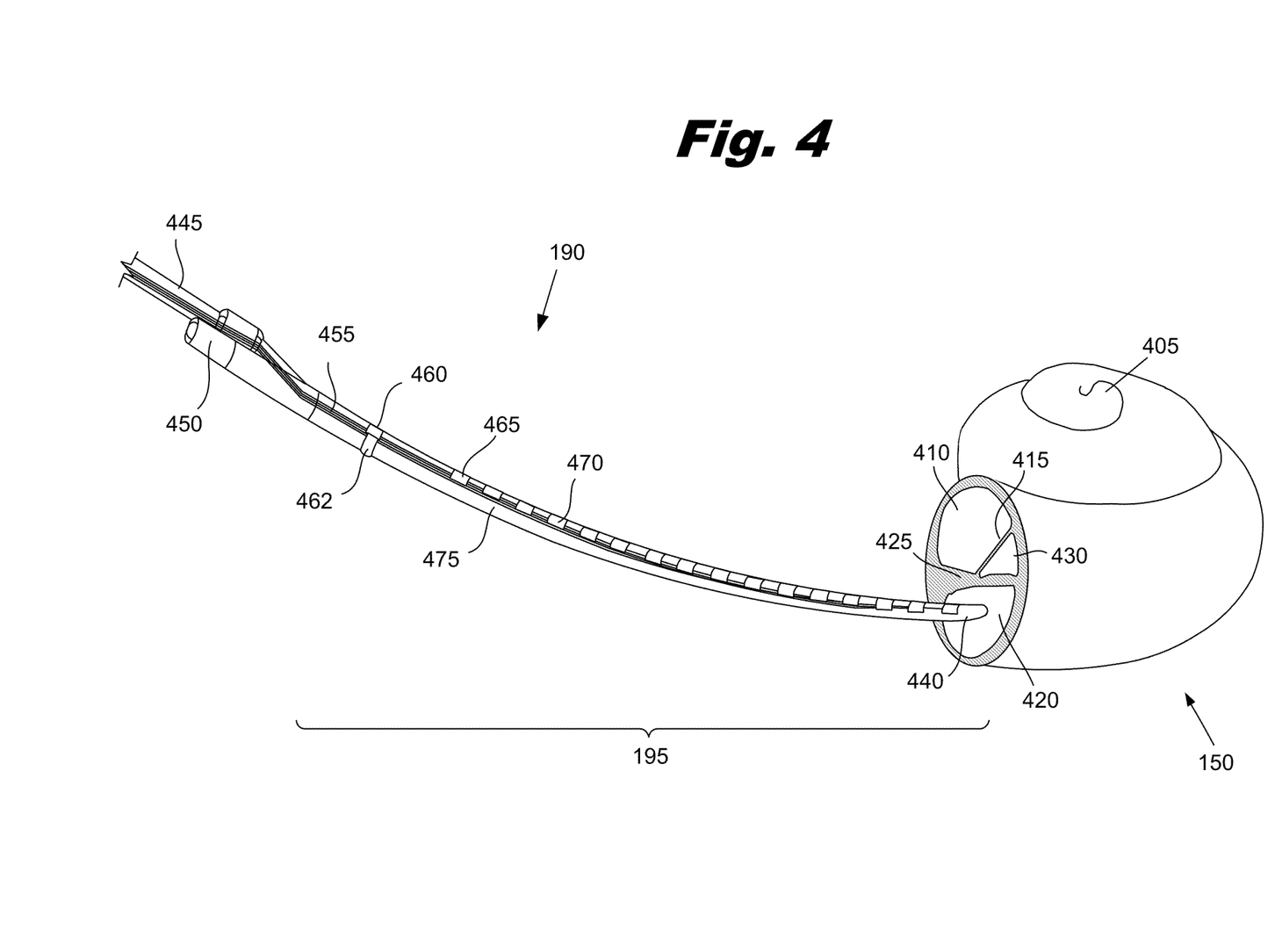
FIG. 4 is a perspective view of an illustrative electrode array being inserted into a cochlea, according to one embodiment of principles described herein.

FIG. 4 is a partially cut away perspective view of a cochlea (150) and shows an illustrative electrode array (195) being inserted into the cochlea (150). The primary structure of the cochlea is a hollow, helically coiled, tubular bone, similar to a nautilus shell. The coiled tube is divided through most of its length into three fluid-filled spaces (scalae). The scala vestibuli (410) is partitioned from the scala media (430) by Reissner's membrane (415) and lies superior to it. The scala tympani (420) is partitioned from the scala media (430) by the basilar membrane (425) and lies inferior to it. A typical human cochlea includes approximately two and a half helical turns of its various constituent channels. The cochlear lead (190) is inserted into one of the scalae, typically the scalae tympani (420), to bring the individual electrodes into close proximity with the tonotopically organized nerves.

The illustrative cochlear lead (190) includes a lead body (445). The lead body (445) connects the electrode array (195) to the internal processor (185, FIG. 3). A number of wires (455) pass through the lead body (445) to bring electrical signals from the internal processor (185, FIG. 3) to the electrode array (195). According to one illustrative embodiment, at the junction of the electrode array (195) to the lead body (445) is a molded silicone rubber feature (450). The feature (450) can serve a variety of functions, including, but not limited to, providing a structure which can be gripped by an insertion tool, providing a visual indicator of how far the cochlear lead (190) has been inserted, and securing the electrode array (195) within the cochlea.

The wires (455) that conduct electrical signals are connected to the electrodes (465, 470) within the electrode array (195). For example, electrical signals which correspond to a low frequency sound may be communicated via a first wire to an electrode near the tip (440) of the electrode array (195). Electrical signals which correspond to a high frequency sound may be communicated by a second wire to an electrode (465) near the base of the electrode array (195). According to one illustrative embodiment, there may be one wire (455) for each electrode (610) within the electrode array (195). The internal processor (185, FIG. 3) may then control the electrical field generated by each electrode individually. For example, one electrode may be designated as a ground electrode. The remainder of the electrodes may then generate electrical fields which correspond to various frequencies of sound. Additionally or alternatively, adjacent electrodes may be paired, with one electrode serving as a ground and the other electrode being actively driven to produce the desired electrical field.

According to one illustrative embodiment, the wires (445) and portions of the electrodes (470) are encased in a flexible body (475). The flexible body (475) may be formed from a variety of biocompatible materials, including, but not limited to medical grade silicone rubber. The flexible body (475) secures and protects the wires (455) and electrodes (465, 470). The flexible body (475) allows the electrode array (195) to bend and conform to the geometry of the cochlea.

Management of the wires during the manufacturing process can be challenging. Typically there will be 16 or more small wires which are formed into a bundle. According to one illustrative embodiment, the electrodes are designed to assist in wire management. However, between the end of the lead body (445) and the first electrode (465), there is a significant distance where there are no electrodes to assist in the wire management. In some embodiments, a dummy electrode (460) is inserted midway between the first electrode (465) and the end of the lead body (445) to assist in wire management. The dummy electrode (460) may also serve as a marker which indicates to the surgeon the current depth of insertion. Additionally, a marker rib (462) may be formed in proximity to the dummy electrode (460) and may serve as an insertion marker.

According to one illustrative embodiment, the dummy electrode (460) may assist in wire management by wrapping around the wires and forming a wire bundle. This can prevent the wires from splaying out and contacting other edges or surfaces during the manufacturing process. Damage to the wires can lead to shorts which may degrade the performance of the cochlear implant.

Figure 5A:
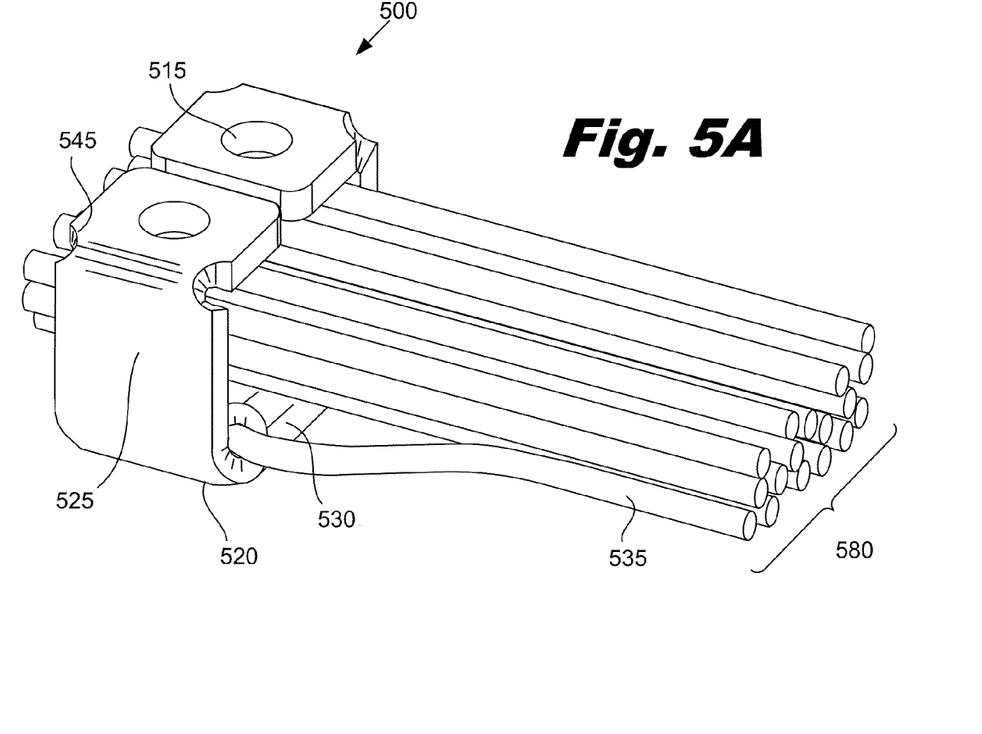
FIGS. 5A and 5B are a perspective view and cross-sectional view, respectively, of one illustrative embodiment of an electrode which shapes a wire bundle, according to one embodiment of principles described herein.

FIG. 5A is a perspective view of one illustrative embodiment of an electrode (500) which assists in wire management. According to one illustrative embodiment, the electrode (500) is formed from a platinum or platinum alloy sheet which is cut and bent into the desired shape. To connect a specific wire to the electrode (500), a flap (530) is folded over the wire (535) associated with this electrode (500) and welded to electrically and mechanically secure it in place. The wings (525) are folded up to secure the wires for the more distal electrodes and form a bundle of wires which passes back along the electrode array, along the cochlear lead and to the integral processor. The wings (525) may have a number of features (545, 515) which assist in bending the wings or securing the electrode in place. The electrode surface (520) is on the underside of the electrode (500). The electrode surface (520) is not covered by the flexible body and is consequently exposed to the body tissues and fluids within the cochlea. The electrode surface (520) is used to generate an electrical field through these tissues, thereby stimulating the adjacent auditory nerve.

Figure 5B:
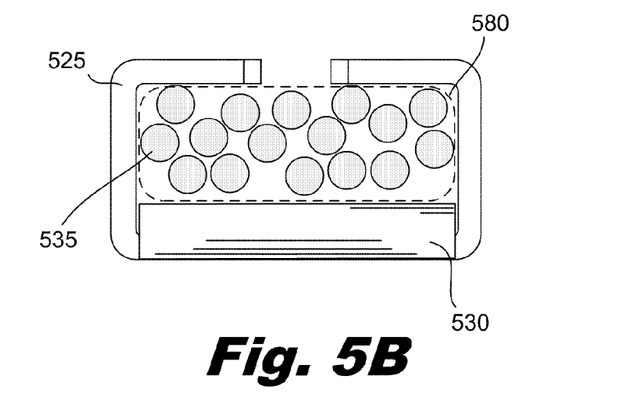

FIG. 5B is a cross-sectional view of the electrode (500) shown in FIG. 5A. Cross-sections of the wires (535) are shown in a wire bundle (580) contained by the wings (525). As discussed above, this wire bundle (580) passes through the entire length of the electrode array (195); however, each individual wire within the bundle terminated at the electrode to which it is welded.

The management of the wire bundle (580) has several goals. For example, one goal is to protect the integrity of the wires and their connections to the electrodes. Another goal may be to shape the wire bundle (580) to influence the overall stiffness of the electrode array (195, FIG. 1). Another goal in wire management may be to reduce the manufacturing complexity and cost of the cochlear implant. Additionally, the proper management of the wire bundle can reduce kinking of the lead and incidences of shorts.

Figure 6A:
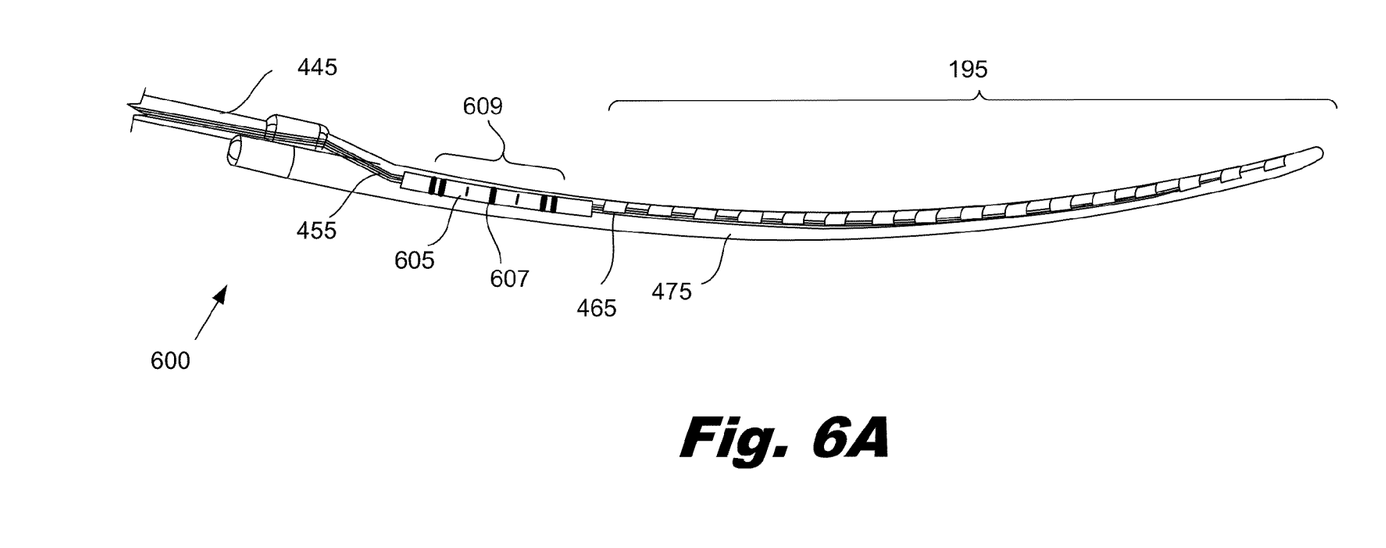
FIG. 6A is a side view of an illustrative cochlear lead which includes an integrated wire carrier, according to one embodiment of principles described herein.

FIG. 6A is a side view of an illustrative cochlear lead (600) which includes an integrated wire carrier (605). In this illustrative embodiment, the integrated wire carrier (605) encloses the wires (455) along a region which extends the location where the wires enter the flexible body (475) to just before the first electrode (465). In one illustrative embodiment, the dummy electrode (460; FIG. 4) and marker rib (462; FIG. 4) are no longer needed because of the integrated wire carrier (605).

According to one illustrative embodiment, the integrated wire carrier (605) may have a number of marks (607) which form an insertion depth scale (609). As the surgeon is inserting the electrode array (195) into the cochlea, these marks (607) could be easily visible through the transparent or translucent silicone which makes up the flexible body (475). The surgeon would then be able to better gauge the depth of insertion or over insertion. For example, a center mark may be the target depth of insertion while marks at the ends of the scale indicate the allowable range of insertion depths. Additionally or alternatively, the scale may allow a surgeon to more precisely personalize the insertion of the electrode into a given cochlea. For example, if a patient has a malformed or partly ossified cochlea, the surgeon may opt not to insert the electrode array as far. The scale (609) would allow the surgeon to more precisely gauge this customized depth.

The marks (607) on the scale (609) may take a variety of forms, colors, thicknesses, and arrangements. According to one illustrative embodiment, the marks on the scale may be formed so that they are visible during X-ray or other non-invasive imaging. The marks (607) could then be used to gage the accuracy of surgical placement, location of the cochleostomy, or the motion of the electrode over time.

Radio-opaque markers formed on the wire carrier (605) are one illustrative method for providing visibility of the marks by non-invasive imaging techniques. For example, the radio-opaque markers could be formed from one or more platinum rings which are crimped around the wire carrier (605). Additionally or alternatively, radio-opaque particles could be incorporated into portions of the wire carrier (605). For example, tantalum or barium sulfate particles could be incorporated into a silicone rubber wire carrier. In an alternative embodiment, the radio opaque marker could be incorporated directly into the flexible body (475).

The integrated wire carrier (605) may have a variety of geometries and be made from a number of different materials. FIGS. 6B-6E are cross-sectional views of illustrative integrated wire carriers (605, 615, 620, 625) which may be used control, shape, and protect the wire bundle (455). The integrated wire carriers may be made from a variety of rigid, semi-rigid, or rigid materials, including plastics, metals, composite materials, or other suitable materials. According to on illustrative embodiment, the integrated wire carrier is formed from polytetrafluoroethylene (PTFE), acetal, such as DuPont™ Delrin® acetal resin, polyaryletheretherketone, (PEEK) or silicone.

Figure 6B:
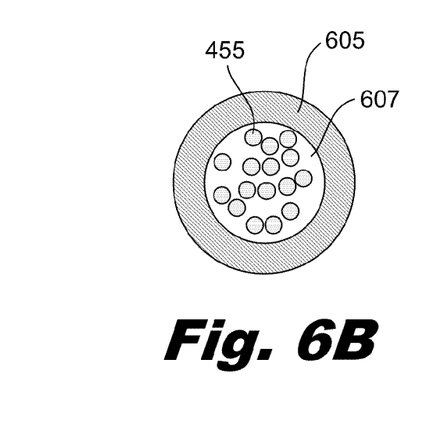
FIGS. 6B-6E are cross-sectional views of illustrative integrated wire carriers, according to one embodiment of principles described herein.

FIG. 6B is a cross sectional view of one illustrative integrated wire carrier which has a circular cross-section with wires (455) which pass through the center opening (607). This design may have a number of advantages including low cost and very good containment of the wires.

Figure 6C:
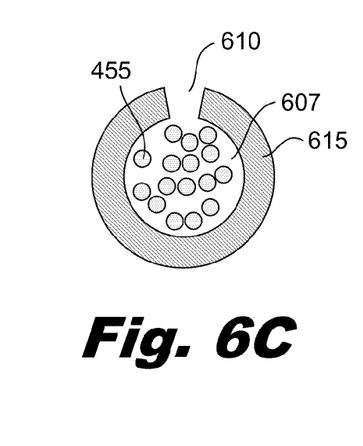
Figure 6D:
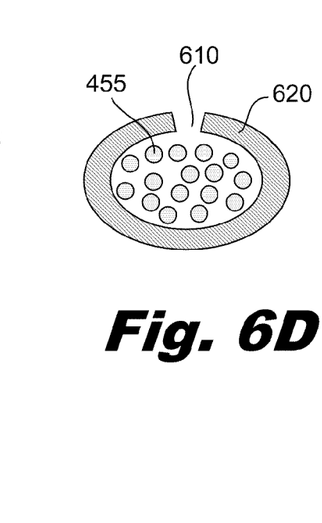

FIG. 6C is a cross-sectional view of one illustrative integrated wire carrier which has a circular cross-section with a slit (610) along one side. The slit (610) may provide some manufacturing advantages as the wires (455) do not need to be threaded through the length of the integrated wire carrier (615). Instead, the wires (455) or wire bundle can be passed through the slit (610) and into the center opening (607). Similarly, FIG. 6D is a cross-sectional view of an illustrative integrated wire carrier (620) which has a hollow elliptical cross-section. The elliptical cross-section may be useful in forming a wire bundle which is similar to the shape the electrodes will define further down the wire bundle. Additionally, the elliptical integrated wire carrier (620) may form a wire bundle which has asymmetric bending stiffness which reduces the bending stress as the electrode is inserted around the spiral interior of the cochlea.

Figure 6E:
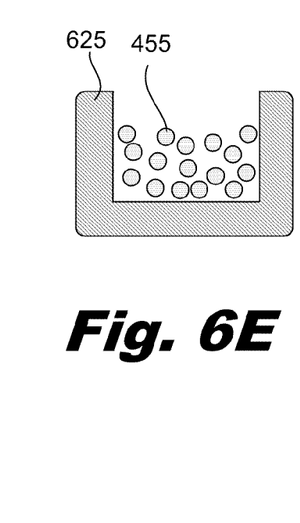

FIG. 6E is a cross-sectional view of a "U" shaped integrated wire carrier (625) which provides containment of the wires (455) on three sides. This may further simplify the manufacturing process because the integrated wire carrier (625) may simply be slipped over the wire bundle.

The integrated wire carrier (605, 615, 620, 625) may have a number of alternative geometries and/or additional features. For example, the composition or wall thickness of the integrated wire carrier may change over its length. Further, the integrated wire carrier may have varying lengths and cover the wires over a different length than that shown in FIG. 6A.

Figure 7:
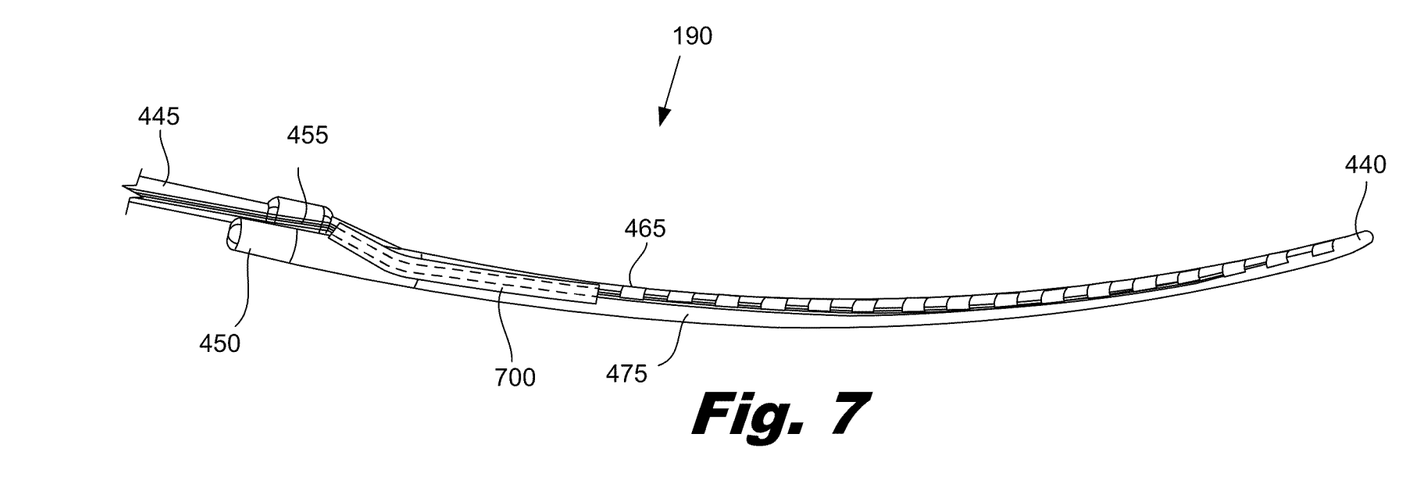
FIG. 7 is a side view of an illustrative cochlear lead which includes an integrated wire carrier, according to one embodiment of principles described herein.

FIG. 7 is a side view of an illustrative cochlear lead (190) which includes an integrated wire carrier (700) which follows the wire bundle (455) as it turns to exit the flexible body (475). Dashed lines show the path of the wire bundle (455) through the integrated wire carrier (700). This extended integrated wire carrier (700) can provide more comprehensive wire management because the wires will be controlled over almost the entire distance between the exit of the lead body (445) and the first electrode (465).

Figure 8:
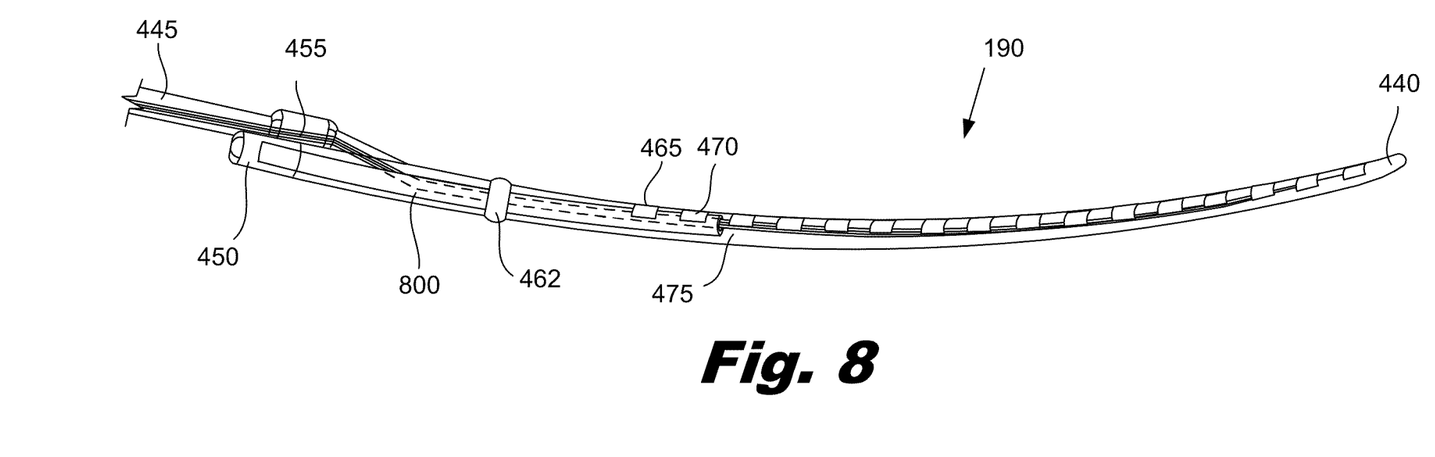
FIG. 8 is a side view of an illustrative cochlear lead which includes an integrated wire carrier, according to one embodiment of principles described herein.

FIG. 8 is a side view of an illustrative cochlear lead (190) which includes an integrated wire carrier (800) which extends into the molded feature (450) and past the first several electrodes (465). In this illustrative embodiment, the integrated wire carrier (800) may have a slit which extends over only a portion of its length. For example, the slit may extend from the entry point of the wire bundle to its exit point. The slit may be wide enough to accommodate the protrusion of the electrodes (465, 470) to the surface of the flexible body (475) and to allow for individual electrode wires to be routed and bonded (e.g. welded) to an electrode. Alternatively, the integrated wire carrier (800) may have a slit along its entire length or other geometry.

The extension of the integrated wire carrier (800) into the molded feature may have a number of benefits, including better securing the integrated wire carrier into place and better control over the integrated wire carrier during the insertion process.

In sum, an integrated wire carrier can provide wire management within the electrode array. This wire management can shape the wire bundle to reduce the potential for damage to the delicate wires, decrease manufacturing costs, and increase the uniformity of the electrode array. A scale on the exterior of the integrated wire carrier can provide information about the insertion depth of the electrode array during surgery or over time.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. A cochlear lead comprising:
   an electrode array comprising a plurality of electrodes configured to stimulate an auditory nerve from within a cochlea;
   a lead body connected to the electrode array;
   a plurality of wires passing through the lead body and connecting to the plurality of electrodes;
   an integrated wire carrier extending between an exit of the wires from the lead body and a first electrode in the electrode array, the integrated wire carrier comprising a cavity along its longitudinal axis configured to contain the plurality of wires and shape the plurality of wires into a wire bundle along the longitudinal axis of the integrated wire carrier; and
   a flexible body encapsulating the integrated wire carrier and the wires.

2. The cochlear lead of claim 1, in which said integrated wire carrier further comprises a slit through a wall of the integrated wire carrier and into the cavity.

3. The cochlear lead of claim 2, in which the slit extends down the entire length of the integrated wire carrier.

4. The cochlear lead of claim 2, in which the slit extends over a partial length of the integrated wire carrier.

5. The cochlear lead of claim 1, in which the integrated wire carrier has a U shaped cross-section.

6. The cochlear lead of claim 1, in which the cross-sectional geometry of the integrated wire carrier varies along its length.

7. The cochlear lead of claim 1, in which the material properties of the integrated wire carrier vary along its length.

8. The cochlear lead of claim 1, further comprising an insertion depth scale on an outer surface of the integrated wire carrier.

9. The cochlear lead of claim 8, in which the insertion depth scale comprises at least one radio-opaque mark.

10. The cochlear lead of claim 1, further comprising a molded gripping feature, the integrated wire carrier extending into the molded gripping feature.

11. The cochlear lead of claim 1, further comprising a cochleostomy marker rib molded around the integrated wire carrier.

12. The cochlear lead of claim 1, in which the integrated wire carrier extends only part way through the electrode array.

13. The cochlear lead of claim 1, in which the integrated wire carrier extends past the first electrode.

14. The cochlear lead of claim 8, in which the insertion depth scale is configured to show insertion depth of the cochlear electrode array into a cochlea.

15. The cochlear lead of claim 8, in which the insertion depth scale comprises:
    a center mark indicating a target depth of insertion to the cochlea; and
    marks on either side of the center mark defining an allowable range of insertion depths.

16. The cochlear lead of claim 8, in which flexible body comprises transparent or translucent silicone through which the insertion depth scale is visible.

17. The cochlear lead of claim 9, in which the at east one radio-opaque marker comprises at least one platinum ring around the wire carrier.

18. The cochlear lead of claim 9, in which the at least one radio-opaque marker comprises tantalum or barium sulfate particles incorporated into the integrated wire carrier.

19. The cochlear lead of claim 10, in which the integrated wire carrier has a solid proximal cross-section and a hollow distal cross-section, the proximal end of the integrated wire carrier being formed in the molded gripping feature and the distal end of the integrated wire carrier extending into the electrode array.

20. A cochlear lead comprising:
    an electrode array comprising a plurality of electrodes configured to stimulate an auditory nerve from within a cochlea, each of the electrodes comprising wings;
    a lead body connected to the electrode array;
    a plurality of wires passing through the lead body and connecting to the plurality of electrodes, in which a first wire is connected to a first electrode and wires connecting to distal electrodes passing over the first electrode, the wings on the first electrode folding upward to enclose the wires passing over the first electrode to form a wire bundle;
    an integrated wire carrier with a cavity along its longitudinal axis configured to contain the plurality of wires and shape said plurality of wires into the wire bundle along the longitudinal axis, the integrated wire carrier extending between the lead body and the first electrode in the electrode array, the integrated wire carrier further comprising:
        a slit through a wall of the integrated wire carrier, the slit extending along at least a portion of the integrated wire carrier;
        a radio-opaque center mark indicating a target insertion depth into the cochlea, the radio-opaque center mark comprising a platinum alloy ring;
        marks on either side of the center mark defining an allowable range of insertion depths; and
    a flexible body encapsulating the integrated wire carrier and the wires, the flexible body being formed from transparent or translucent silicone such that the integrated wire carrier is visible through the flexible body.

* * * * *